United States Patent
Hsiung et al.

(10) Patent No.: US 11,680,893 B2
(45) Date of Patent: Jun. 20, 2023

(54) IDENTIFICATION USING SPECTROSCOPY

(71) Applicant: VIAVI Solutions Inc., San Jose, CA (US)

(72) Inventors: Changmeng Hsiung, Redwood City, CA (US); Christopher G. Pederson, Santa Rosa, CA (US); Peng Zou, Ridgefield, CT (US); Lan Sun, Santa Rosa, CA (US)

(73) Assignee: VIAVI Solutions Inc., Chandler, AZ (US)

(*) Notice: Subject to any disclaimer, the term of this patent is extended or adjusted under 35 U.S.C. 154(b) by 1059 days.

(21) Appl. No.: 16/405,050

(22) Filed: May 7, 2019

(65) Prior Publication Data

US 2019/0257746 A1    Aug. 22, 2019

Related U.S. Application Data

(63) Continuation of application No. 15/247,554, filed on Aug. 25, 2016, now Pat. No. 10,309,894.
(Continued)

(51) Int. Cl.
*G01N 33/48* (2006.01)
*G01N 33/50* (2006.01)
(Continued)

(52) U.S. Cl.
CPC ............... *G01N 21/31* (2013.01); *G06N 7/01* (2023.01); *G06N 20/00* (2019.01); *G06N 20/10* (2019.01); *G16C 20/20* (2019.02); *G16C 20/70* (2019.02)

(58) Field of Classification Search
CPC ........ G01N 21/31; G06N 7/005; G06N 20/00; G06N 20/10; G16C 20/20; G16C 20/70; G01J 3/28
See application file for complete search history.

(56) References Cited

U.S. PATENT DOCUMENTS 3,818,197 A  *  6/1974  Piccolo ................ G01J 3/02
                                                    356/306
9,087,303 B2     7/2015  Rinott et al.
(Continued)

FOREIGN PATENT DOCUMENTS

| CN | 101135639 A | 3/2008 |
|----|-------------|--------|
| CN | 103003814 A | 3/2013 |

(Continued)

OTHER PUBLICATIONS

Vrabie et al. Independent component analysis of Raman spectra: Application on paraffin-embedded skin biopsies. Biomedical Signal Processing and Control, vol. 2, pp. 40-50. (Year: 2007).*
(Continued)

*Primary Examiner* — Russell S Negin
(74) *Attorney, Agent, or Firm* — Harrity & Harrity, LLP

(57) ABSTRACT

A device may receive information identifying results of a spectroscopic measurement of an unknown sample. The device may perform a first classification of the unknown sample based on the results of the spectroscopic measurement and a global classification model. The device may generate a local classification model based on the first classification. The device may perform a second classification of the unknown sample based on the results of the spectroscopic measurement and the local classification model. The device may provide information identifying a class associated with the unknown sample based on performing the second classification.

21 Claims, 11 Drawing Sheets

Related U.S. Application Data

(60) Provisional application No. 62/210,198, filed on Aug. 26, 2015.

(51) Int. Cl.
  *G01N 21/31* (2006.01)
  *G06N 20/00* (2019.01)
  *G16C 20/20* (2019.01)
  *G06N 20/10* (2019.01)
  *G06N 7/01* (2023.01)
  *G16C 20/70* (2019.01)

(56) References Cited

U.S. PATENT DOCUMENTS

| | | | |
|---|---|---|---|
| 10,309,894 B2* | 6/2019 | Hsiung | G01N 21/31 |
| 2005/0228591 A1 | 10/2005 | Hur | |
| 2010/0036795 A1 | 2/2010 | Busch et al. | |
| 2010/0062547 A1* | 3/2010 | Hadidi | H01J 37/32935 |
| | | | 118/712 |
| 2010/0179934 A1 | 7/2010 | Howley et al. | |
| 2010/0241598 A1 | 9/2010 | Yuta et al. | |
| 2011/0286628 A1 | 11/2011 | Goncalves et al. | |
| 2013/0279794 A1 | 10/2013 | Greenberg et al. | |
| 2014/0188781 A1 | 7/2014 | Fawaz et al. | |
| 2015/0051840 A1 | 2/2015 | Vervier et al. | |
| 2015/0066377 A1 | 3/2015 | Parchen et al. | |
| 2015/0220853 A1 | 8/2015 | Marcheret | |
| 2015/0370889 A1 | 12/2015 | Chiba | |
| 2017/0059480 A1 | 3/2017 | Hsiung et al. | |

FOREIGN PATENT DOCUMENTS

| | | |
|---|---|---|
| CN | 103258239 A | 8/2013 |
| CN | 103425991 A | 12/2013 |
| CN | 103488874 A | 1/2014 |
| CN | 103903012 A | 7/2014 |
| EP | 1992939 A1 | 11/2008 |
| JP | 2010527017 A | 8/2010 |
| JP | 2011094982 A | 5/2011 |
| JP | 2015516570 A | 6/2015 |
| JP | 2015522249 A | 8/2015 |
| WO | 2009078096 A1 | 6/2009 |
| WO | 2014136327 A1 | 9/2014 |

OTHER PUBLICATIONS

Gowen et al., "Recent Applications of Chemical Imaging to Pharmaceutical Process Monitoring and Quality Control," European Journal of Pharmaceutics and Biopharmaceutics, May 2008, vol. 69(1), pp. 10-22.

Bergstrom C.A.S., et al., "Global and Local Computational Models for Aqueous Solubility Prediction of Drug-Like Molecules," Journal of chemical information and computer sciences, Mar. 11, 2004, vol. 44, pp. 1477-1488.

Extended European Search Report for Application No. EP16185432, dated Jan. 2, 2017, 9 pages.

Leek J.T., et al., "Tackling the Widespread and Critical Impact of Batch Effects in High-throughput Data," Nature Reviews: Genetics, 2010, vol. 11, pp. 733-739.

Pierna F., et al., "Combination of Support Vector Machines (SVM) and Near-Infrared (NIR) Imaging Spectroscopy for the Detection of Meat and Bone Meal (MBM) in Compound Feeds," Journal of Chemometrics, vol. 18(7-8), Dec. 21, 2004, pp. 341-349.

Prieto N., et al., "Application of Near Infrared Reflectance Spectroscopy to Predict Meat and Meat Products Quality: A Review,"Meat Sience , 2009, vol. 83, pp. 175-186.

Sun L., et al., "Pharmaceutical Raw Material Identification Using Miniature Near-Infrared (MicroNIR) Spectroscopy and Supervised Pattern Recognition Using Support Vector Machine," https://www.ncbi.nlm.nih.gov/pmc/articles/PMC4871175/, Mar. 30, 2016, 11 pages.

Guodong et al., "Hierarchical Learning Strategy in Semantic Relation Extraction," Information Processing and Management, Aug. 2007, vol. 44, pp. 1008-1021.

Ma and Wang., "Simultaneous Characterization of Multiple Properties of Solid and Liquid Phases in Crystallization Processes Using NIR," Particuology, Aug. 2011, vol. 9, pp. 589-597. [Retrieved from: doi:10.1016/j.partic.2011.03.010].

Extended European Search Report for Application No. EP20217282.1, dated Apr. 12, 2021, 9 pages.

* cited by examiner

IDENTIFICATION USING SPECTROSCOPY

RELATED APPLICATION

This application claims priority under 35 U.S.C. § 119 to U.S. Provisional Patent Application No. 62/210,198 filed on Aug. 26, 2015, the content of which is incorporated by reference herein in its entirety.

BACKGROUND

Raw material identification may be utilized for quality-control of pharmaceutical products. For example, raw material identification may be performed on a medical compound to determine whether component ingredients of the medical compound correspond to a packaging label associated with the medical compound. Spectroscopy may facilitate non-destructive raw material identification with reduced preparation and data acquisition time relative to other chemistry techniques.

SUMMARY

According to some possible implementations, a device may include one or more processors. The one or more processors may receive information identifying results of a spectroscopic measurement of an unknown sample. The one or more processors may perform a first classification of the unknown sample based on the results of the spectroscopic measurement and a global classification model. The global classification model may utilize a support vector machine (SVM) classifier technique. The global classification model may include a global set of classes. The one or more processors may generate a local classification model based on the first classification. The local classification model may utilize the SVM classifier technique. The local classification model may include a subset of classes of the global set of classes. The one or more processors may perform a second classification of the unknown sample based on the results of the spectroscopic measurement and the local classification model. The one or more processors may provide information identifying a class, of the subset of classes, associated with the unknown sample based on performing the second classification.

According to some possible implementations, a computer-readable medium may store instructions, that when executed by one or more processors, may cause the one or more processors to receive information identifying results of a set of spectroscopic measurements of an unknown set. The unknown set may include a set of unknown samples. The one or more instructions, when executed by one or more processors, may cause the one or more processors to perform a first classification of the set of unknown samples based on the results of the set of spectroscopic measurements and a global classification model. The global classification model may utilize a support vector machine (SVM) linear classifier technique. The one or more instructions, when executed by one or more processors, may cause the one or more processors to generate a set of local classification models for the set of unknown samples based on the first classification. The set of local classification models may utilize the SVM linear classifier technique. The one or more instructions, when executed by one or more processors, may cause the one or more processors to perform a second classification of the set of unknown samples based on the results of the set of spectroscopic measurements and the set of local classification models. The one or more instructions, when executed by one or more processors, may cause the one or more processors to provide information identifying classifications of the set of unknown samples based on performing the second classification.

According to some possible implementations, a method may include receiving, by a device, information identifying results of a spectroscopic measurement of an unknown sample performed by a first spectrometer. The method may include performing, by the device, a first classification of the unknown sample based on the results of the spectroscopic measurement and a global classification model. The global classification model may be generated by utilizing a support vector machine (SVM) classifier technique and a set of spectroscopic measurements performed by a second spectrometer. The method may include generating, by the device, a local classification model based on the first classification. The local classification model may utilize the SVM classifier technique. The local classification model may include a subset of classes of a set of classes of the global classification model. The method may include performing by the device, a second classification of the unknown sample based on the results of the spectroscopic measurement and the local classification model. The method may include providing, by the device, information identifying a class, of the subset of classes, associated with the unknown sample based on performing the second classification.

DETAILED DESCRIPTION

The following detailed description of example implementations refers to the accompanying drawings. The same reference numbers in different drawings may identify the same or similar elements.

Raw material identification (RMID) is a technique utilized to identify components (e.g., ingredients) of a particular sample for identification, verification, or the like. For example, RMID may be utilized to verify that ingredients in a pharmaceutical compound correspond to a set of ingredients identified on a label. A spectrometer may be utilized to perform spectroscopy on a sample (e.g., the pharmaceutical compound) to determine components of the sample. The spectrometer may determine a set of measurements of the sample and may provide the set of measurements for classification. A chemometric classification technique (e.g., a classifier) may facilitate determination of the components of the sample based on the set of measurements of the sample. However, some chemometric classification techniques may be associated with poor transferability, insufficient granularity for performing large-scale classification, or the like, relative to other techniques. Implementations, described herein, may utilize a hierarchical support vector machine classifier to facilitate RMID. In this way, a control device of a spectrometer facilitates improved classification accuracy relative to other RMID techniques.

Figure 1A:
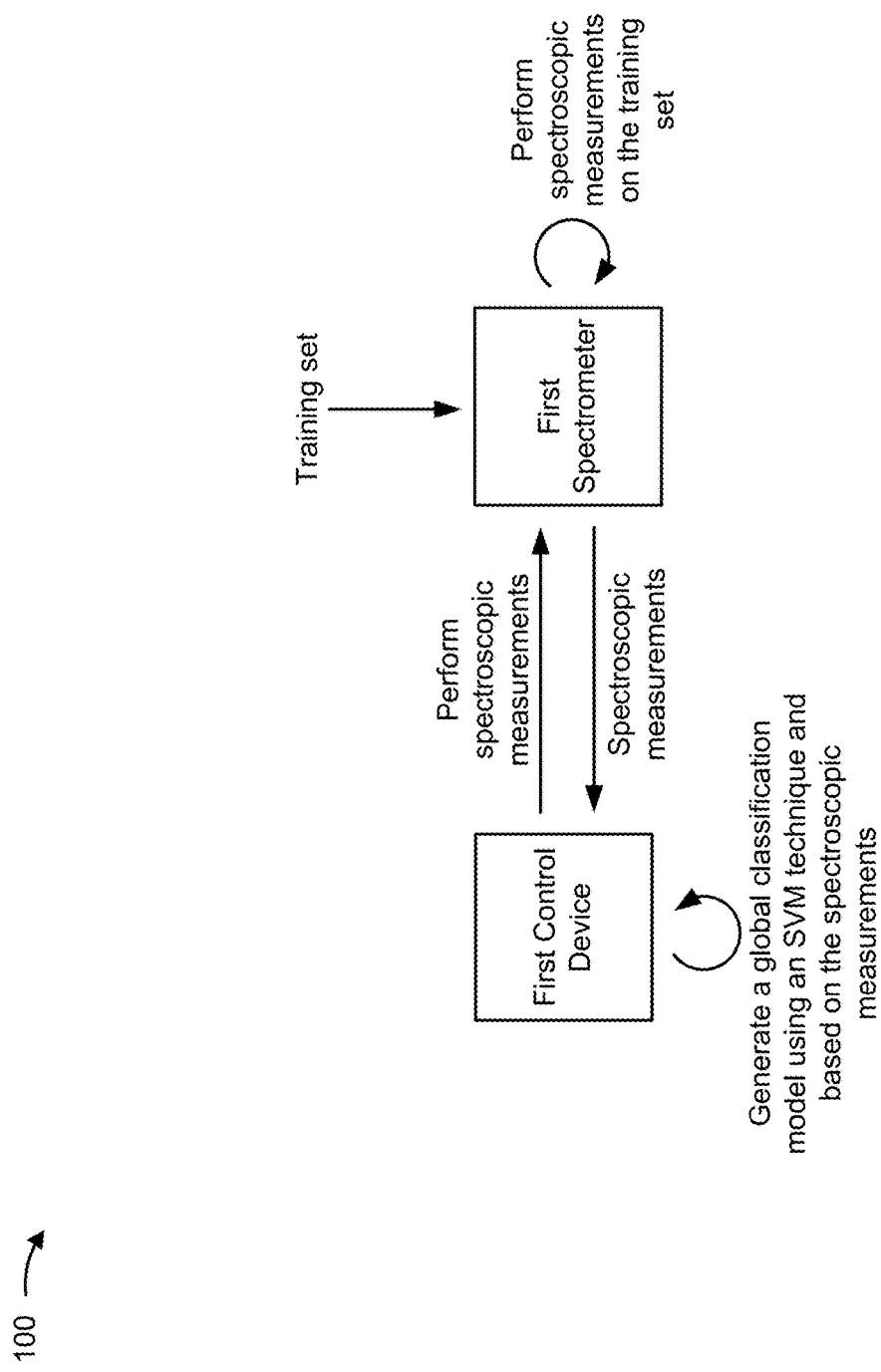
FIGS. 1A and 1B are diagrams of an overview of an example implementation described herein.
Figure 1B:
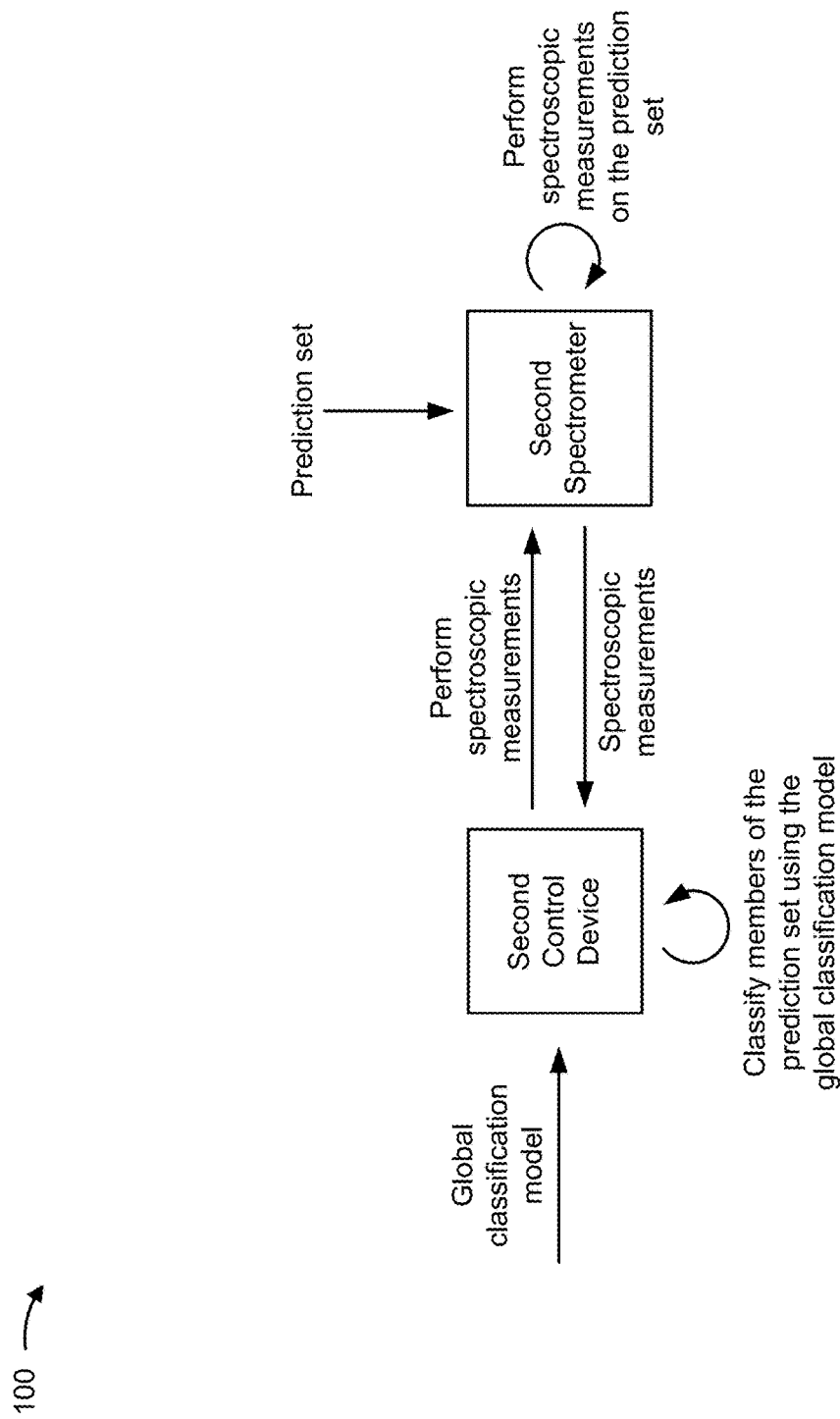

FIGS. 1A and 1B are diagrams of an overview of an example implementation 100 described herein. As shown in FIG. 1A, example implementation 100 may include a first control device and a first spectrometer. The first control device may cause the first spectrometer to perform a set of spectroscopic measurements on a training set (e.g., a set of known samples utilized for training a classification model). The training set may be selected to include a threshold quantity of samples for each class of the classification model. A class of the classification model may refer to a grouping of similar compounds that share one or more characteristics in common, such as (in a pharmaceutical context) lactose compounds, fructose compounds, acetaminophen compounds, ibuprofen compounds, aspirin compounds, or the like.

As further shown in FIG. 1A, the first spectrometer may perform the set of spectroscopic measurements on the training set based on receiving an instruction from the first control device. For example, the first spectrometer may determine a spectrum for each sample of the training set. The first spectrometer may provide the set of spectroscopic measurements to the first control device. The first control device may generate a global classification model using a particular classification technique and based on the set of spectroscopic measurements. For example, the first control device may generate the global classification model using a support vector machine (SVM) technique (e.g., a machine learning technique for information classification). The global classification model may include information associated with assigning a particular spectrum to a particular class, and may include information associated with identifying a type of compound that is associated with the particular class. In this way, a control device can provide information identifying a type of compound of an unknown sample based on assigning a spectrum of the unknown sample to a particular class. The global classification model may be stored via a data structure, provided to one or more other control devices, or the like.

As shown in FIG. 1B, a second control device may receive the global classification model (e.g., from the first control device), and may store the global classification model via a data structure. The second control device may cause a second spectrometer to perform a set of spectroscopic measurements on an unknown set (e.g., a set of unknown samples for which RMID is to be performed). The second spectrometer may perform the set of spectroscopic measurements based on receiving an instruction from the second control device. For example, the second spectrometer may determine a spectrum for each sample of the unknown set. The second spectrometer may provide the set of spectroscopic measurements to the second control device. The second control device may perform RMID on the unknown set based on the global classification model using a multi-stage classification technique.

With regard to FIG. 1B, the second control device may perform a first classification of a particular sample of the unknown set using the global classification model. The second control device may determine a set of confidence metrics associated with the particular sample and the global classification model. A confidence metric may refer to a confidence associated with assigning the particular sample to a particular class. For example, the second control device may determine a confidence metric associated with the particular sample and each class of the global classification model. The second control device may select a subset of classes of the global classification model based on the one or more respective confidence metrics, and may generate a local classification model based on the set of classes. The local classification model may refer to an in situ classification model that is generated using the SVM technique and the subset of classes. The second control device may perform a second classification based on the local classification model to assign the particular sample to a particular class. In this way, the second control device performs RMID for a particular sample of the unknown set with improved accuracy relative to other classification models and/or single stage classification techniques. The second control device may perform a first classification and a second classification for each sample of the unknown set to identify each sample of the unknown set. In another example, the first control device may classify the particular sample using a global classification model and a local classification model based on spectroscopy performed by the first spectrometer.

Figure 2:
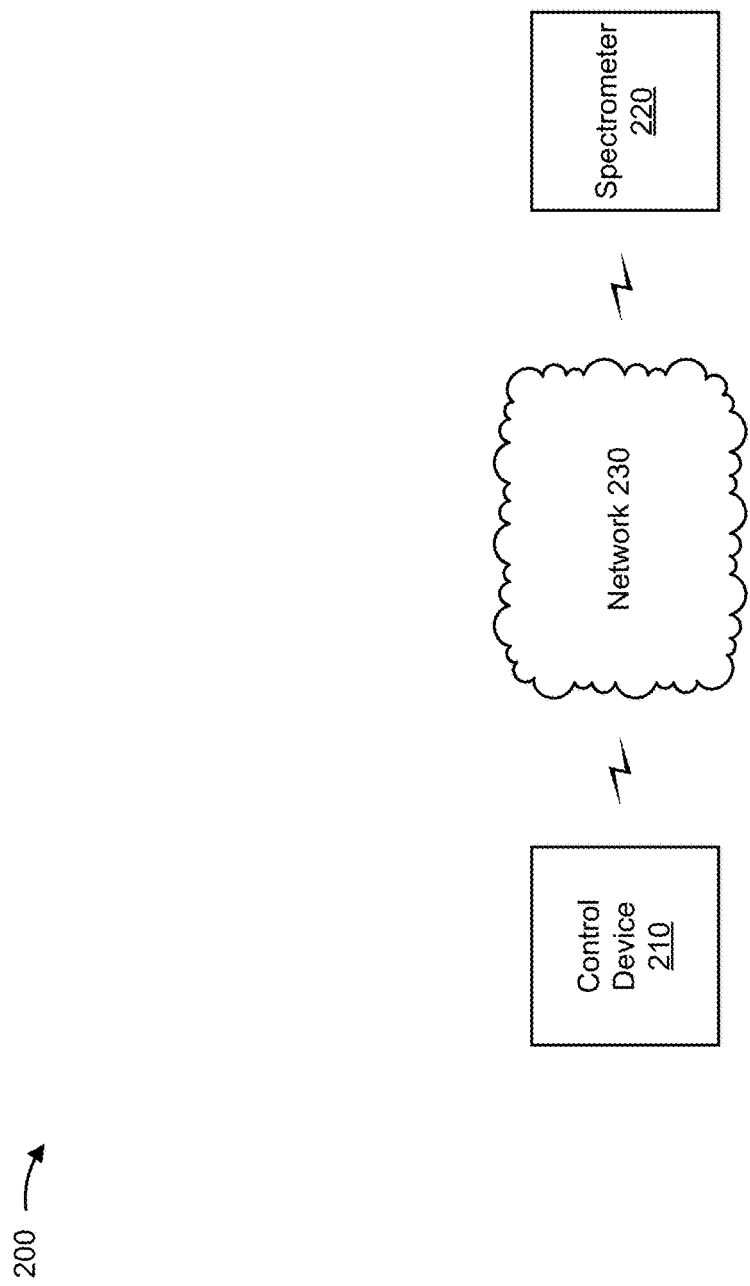
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a control device 210, a spectrometer 220, and a network 230. Devices of environment 200 may interconnect via wired connections, wireless connections, or a combination of wired and wireless connections.

Control device 210 may include one or more devices capable of storing, processing, and/or routing information associated with RMID. For example, control device 210 may include a server, a computer, a wearable device, a cloud computing device, or the like that generates a model based on a classifier and a set of measurements of a training set, and utilizes the model to perform RMID based on a set of measurements of an unknown set. In some implementations, control device 210 may be associated with a particular spectrometer 220. In some implementations, control device 210 may be associated with multiple spectrometers 220. In some implementations, control device 210 may receive information from and/or transmit information to another device in environment 200, such as spectrometer 220.

Spectrometer 220 may include one or more devices capable of performing a spectroscopic measurement on a sample. For example, spectrometer 220 may include a spectrometer device that performs spectroscopy (e.g., vibrational spectroscopy, such as a near infrared (NIR) spectrometer, a mid-infrared spectroscopy (mid-IR), Raman spectroscopy, or the like). In some implementations, spectrometer 220 may be incorporated into a wearable device, such as a wearable spectrometer or the like. In some implementations, spectrometer 220 may receive information from and/or transmit information to another device in environment 200, such as control device 210.

Network 230 may include one or more wired and/or wireless networks. For example, network 230 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. For example, although control device 210 and spectrometer 220 are described, herein, as being two separate devices, control device 210 and spectrometer 220 may be implemented within a single device. Additionally, or alternatively, a set of devices (e.g., one or more devices) of environment 200 may perform one or more functions described as being performed by another set of devices of environment 200.

Figure 3:
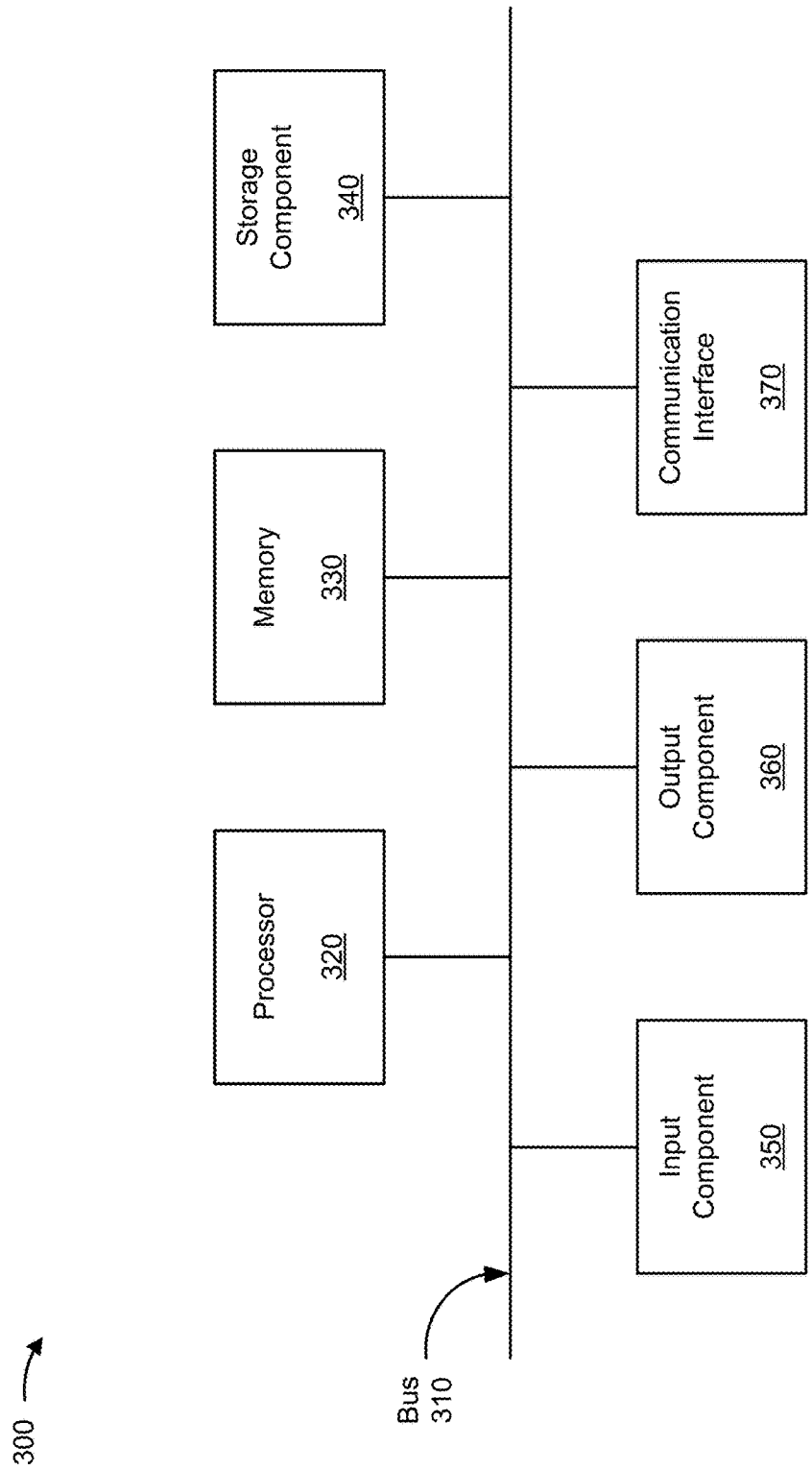
FIG. 3 is a diagram of example components of one or more devices of FIG. 2.

FIG. 3 is a diagram of example components of a device 300. Device 300 may correspond to control device 210 and/or spectrometer 220. In some implementations, control device 210 and/or spectrometer 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 is implemented in hardware, firmware, or a combination of hardware and software. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an application-specific integrated circuit (ASIC), etc.) that interprets and/or executes instructions. In some implementations, processor 320 may include one or more processors that can be programmed to perform a function. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 350 may include a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
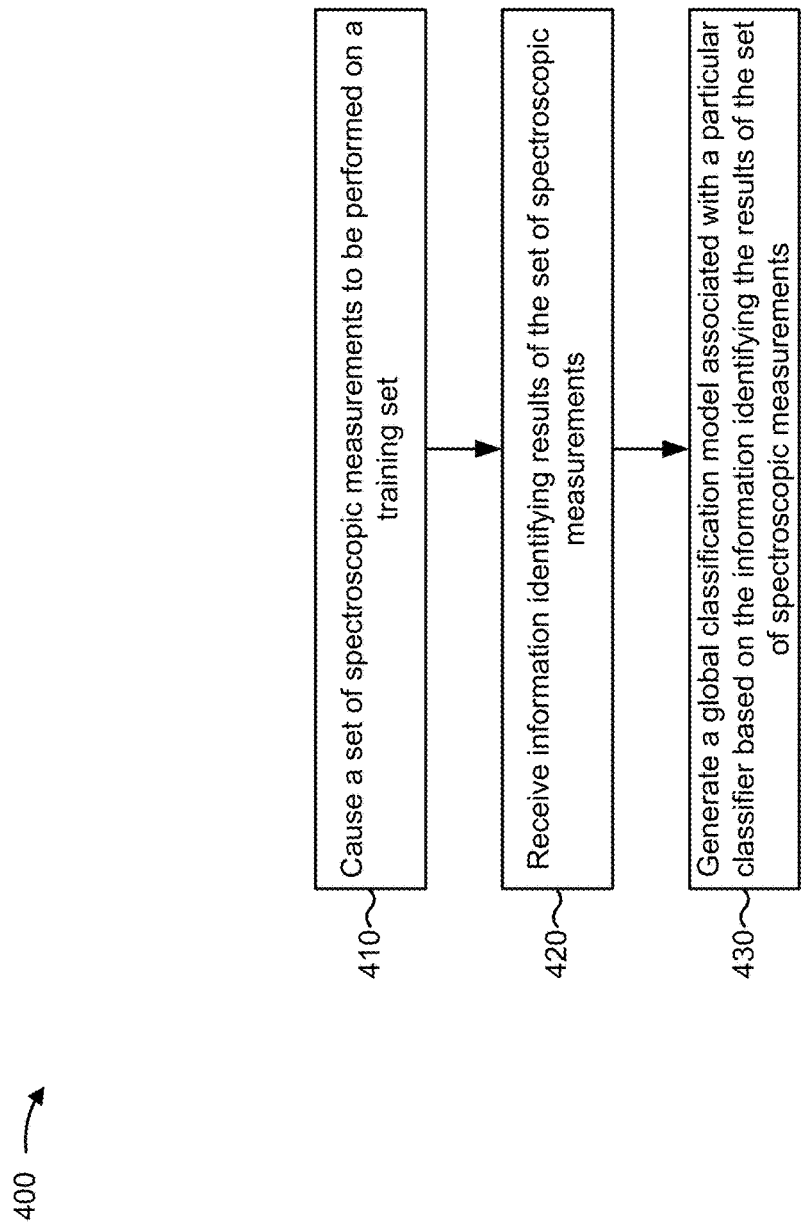
FIG. 4 is a flow chart of an example process for generating a global classification model for raw material identification based on a support vector machine classifier.

FIG. 4 is a flow chart of an example process 400 for generating a global classification model for raw material identification based on a support vector machine classifier. In some implementations, one or more process blocks of FIG. 4 may be performed by control device 210. In some implementations, one or more process blocks of FIG. 4 may be performed by another device or a group of devices separate from or including control device 210, such as spectrometer 220.

As shown in FIG. 4, process 400 may include causing a set of spectroscopic measurements to be performed on a training set (block 410). For example, control device 210 may cause spectrometer 220 to perform a set of spectroscopic measurements on a training set of samples to determine a spectrum for each sample of the training set. The training set may refer to a set of samples of one or more known compounds, which are utilized to generate a global classification model. For example, the training set may include one or more versions of a set of compounds (e.g., one or more versions manufactured by different manufacturers to control for manufacturing differences). In some implementations, the training set may be selected based on an expected set of compounds for which RMID is to be performed. For example, when RMID is expected to be performed for pharmaceutical compounds, the training set may include a set of samples of active pharmaceutical ingredients (APIs), excipients, or the like. In some implementations, the training set may be selected to include a particular quantity of samples for each type of compound. For example, the training set may be selected to include multiple samples (e.g., 5 samples, 10 samples, 15 samples, 50 samples, etc.) of a particular compound. In this way, control device 210 can be provided with a threshold quantity of spectra associated with a particular type of compound, thereby facilitating generation of a class, for a classification model (e.g., a global classification model, a local classification model, etc.), to which unknown samples can be accurately assigned.

In some implementations, control device 210 may cause multiple spectrometers 220 to perform the set of spectroscopic measurements to account for one or more physical conditions. For example, control device 210 may cause a first spectrometer 220 and a second spectrometer 220 to perform a set of vibrational spectroscopic measurements using NIR spectroscopy. Additionally, or alternatively, control device 210 may cause the set of spectroscopic measurements to be performed at multiple times, in multiple locations, under multiple different laboratory conditions, or the like. In this way, control device 210 reduces a likelihood that a spectroscopic measurement is inaccurate as a result of a physical condition relative to causing the set of spectroscopic measurements to be performed by a single spectrometer 220.

As further shown in FIG. 4, process 400 may include receiving information identifying results of the set of spectroscopic measurements (block 420). For example, control device 210 may receive information identifying the results of the set of spectroscopic measurements. In some implementations, control device 210 may receive information identifying a set of spectra corresponding to samples of the training set. For example, control device 210 may receive information identifying a particular spectrum, which was observed when spectrometer 220 performed spectroscopy on the training set. Additionally, or alternatively, control device 210 may receive other information as results of the set of spectroscopic measurements. For example, control device 210 may receive information associated with identifying an absorption of energy, an emission of energy, a scattering of energy, or the like.

In some implementations, control device 210 may receive the information identifying the results of the set of spectroscopic measurements from multiple spectrometers 220. For example, control device 210 may control for physical conditions, such as a difference between the multiple spectrometers 220, a potential difference in a lab condition, or the like, by receiving spectroscopic measurements performed by multiple spectrometers 220, performed at multiple different times, performed at multiple different locations, or the like.

As further shown in FIG. 4, process 400 may include generating a global classification model associated with a particular classifier based on the information identifying the results of the set of spectroscopic measurements (block 430). For example, control device 210 may generate the global classification model associated with an SVM classifier technique based on the information identifying the results of the set of spectroscopic measurements. In some implementations, control device 210 may perform a set of classifications to generate the global classification model. For example, control device 210 may assign a set of spectra, identified by the results of the set of spectroscopic measurements, into a set of classes based on using an SVM technique.

SVM may refer to a supervised learning model that performs pattern recognition for classification. In some implementations, control device 210 may utilize a particular type of kernel function when generating the global classification model using the SVM technique. For example, control device 210 may utilize a radial basis function (RBF) (e.g., termed SVM-rbf) type of kernel function, a linear function (e.g., termed SVM-linear and termed hier-SVM-linear when utilized for a multi-stage classification technique) type of kernel function, a sigmoid function type of kernel function, a polynomial function type of kernel function, an exponential function type of kernel function, or the like. In some implementations, control device 210 may utilize a particular type of SVM, such as a probability value based SVM (e.g., classification based on determining a probability that a sample is a member of a class of a set of classes), a decision value based SVM (e.g., classification utilizing a decision function to vote for a class, of a set of classes, as being the class of which the sample is a member), or the like.

In some implementations, control device 210 may select the particular classifier that is to be utilized for generating the global classification model from a set of classification techniques. For example, control device 210 may generate multiple classification models corresponding to multiple classifiers and may test the multiple classification models, such as by determining a transferability of each model (e.g., an extent to which a classification model generated based on spectroscopic measurements performed on a first spectrometer 220 is accurate when applied to spectroscopic measurements performed on a second spectrometer 220), a large-scale classification accuracy (e.g., an accuracy with which a classification model can be utilized to concurrently classify a quantity of samples that satisfy a threshold), or the like. In this case, control device 210 may select an SVM classifier (e.g., hier-SVM-linear) based on determining that the SVM classifier is associated with superior transferability and/or large-scale classification accuracy relative to other classifiers.

In some implementations, control device 210 may generate the global classification model based on information identifying samples of the training set. For example, control device 210 may utilize the information identifying the types of compounds represented by samples of the training set to identify classes of spectra with types of compounds. In some implementations, control device 210 may train the global classification model when generating the global classification model. For example, control device 210 may cause the model to be trained using a portion of the set of spectroscopic measurements. Additionally, or alternatively, control device 210 may perform an assessment of the global classification model. For example, control device 210 may verify the global classification model (e.g., for predictive strength) utilizing another portion of the set of spectroscopic measurements. In some implementations, control device 210 may verify the global classification model using a multi-stage classification technique. For example, control device 210 may determine that the global classification model is accurate when utilized in association with one or more local classification models, as described herein with regard to FIG. 6. In this way, control device 210 ensures that the global classification model is generated with a threshold accuracy prior to providing the global classification model for utilization by other control devices 210 associated with other spectrometers 220.

In some implementations, control device 210 may provide the global classification model to the other control devices 210 associated with the other spectrometers 220 after generating the global classification model. For example, a first control device 210 may generate the global classification model and may provide the global classification model to a second control device 210 for utilization. In this case, the second control device 210 may store the global classification model, and may utilize the global classification model in generating one or more local classification models and classifying one or more samples of an unknown set, as described herein with regard to FIG. 6. Additionally, or alternatively, control device 210 may store the global classification model for utilization by control device 210 in generating the one or more local classification models and classifying the one or more samples. In this way, control device 210 provides the global classification model for utilization in RMID of unknown samples.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
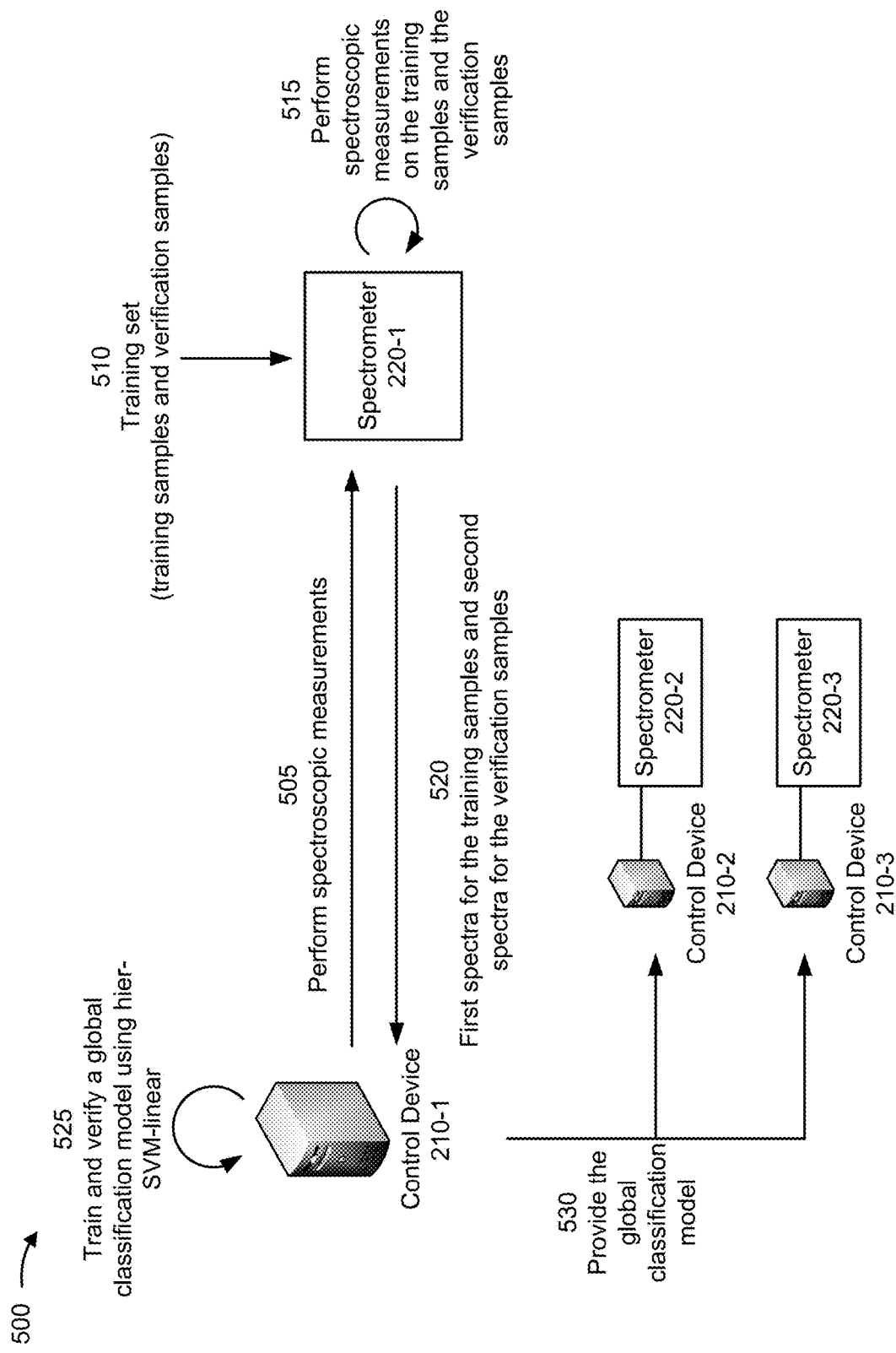
FIG. 5 is a diagram of an example implementation relating to the example process shown in FIG. 4.

FIG. 5 is a diagram of an example implementation 500 relating to example process 400 shown in FIG. 4. FIG. 5 shows an example of generating a global classification model for raw material identification based on a support vector machine classifier.

As shown in FIG. 5, control device 210-1 transmits information to spectrometer 220-1 to instruct spectrometer 220-1 to perform a set of spectroscopic measurements on training set 510. Assume that training set 510 includes a first set of training samples (e.g., measurements of which are utilized for training a global classification model) and a second set of verification samples (e.g., measurements of which are utilized for verifying accuracy of the global classification model). As shown by reference number 515, spectrometer 220-1 performs the set of spectroscopic measurements on the training set based on receiving the instruction. As shown by reference number 520, control device 210-1 receives a first set of spectra for the training samples and a second set of spectra for the verification samples. Assume that control device 210-1 stores information identifying each sample of training set 510.

With regard to FIG. 5, assume that control device 210-1 has selected to utilize a hier-SVM-linear classifier for generating the global classification model (e.g., based on testing the hier-SVM-linear classifier against one or more other classifiers). As shown by reference number 525, control device 210-1 trains the global classification model using the hier-SVM-linear classifier and the first set of spectra and verifies the global classification model using the hier-SVM-linear classifier and the second set of spectra. Assume that control device 210-1 determines that the global classification model satisfies a verification threshold (e.g., has an accuracy that exceeds the verification threshold). As shown by reference number 530, control device 210-1 provides the global classification model to control device 210-2 (e.g., for utilization when performing RMID on spectroscopic measurements performed by spectrometer 220-2) and to control device 210-3 (e.g., for utilization when performing RMID on spectroscopic measurements performed by spectrometer 220-3).

As indicated above, FIG. 5 is provided merely as an example. Other examples are possible and may differ from what was described with regard to FIG. 5.

In this way, control device 210 facilitates generation of a global classification model based on a selected classification technique (e.g., selected based on model transferability, large-scale classification accuracy, or the like) and distribution of the global classification model for utilization by one or more other control devices 210 associated with one or more spectrometers 220. Moreover, control device 210 reduces costs and time requirements relative to generating the global classification model on each control device 210 that is to perform RMID.

Figure 6:
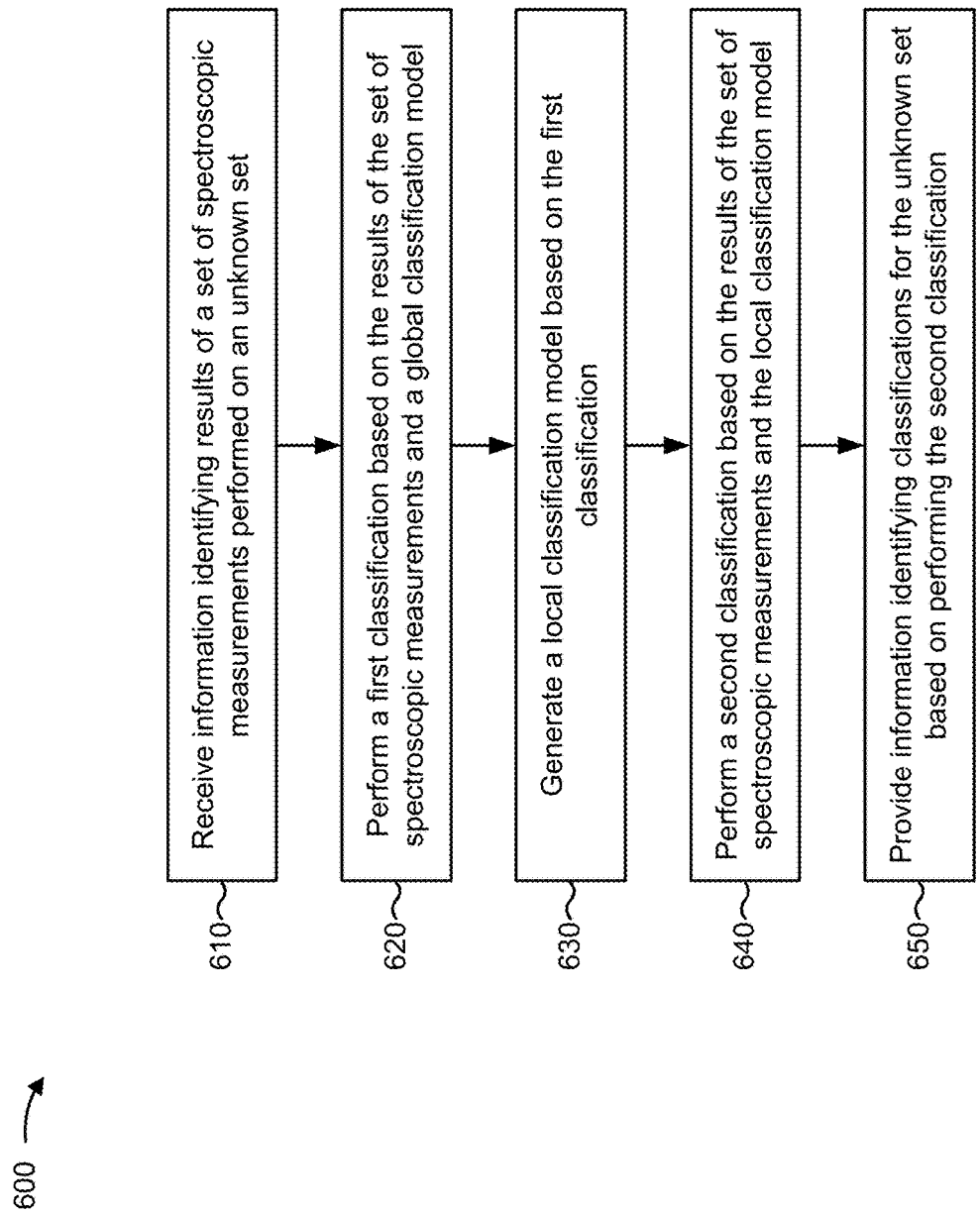
FIG. 6 is a flow chart of an example process for performing raw material identification using a multi-stage classification technique.

FIG. 6 is a flow chart of an example process 600 for performing raw material identification using a multi-stage classification technique. In some implementations, one or more process blocks of FIG. 6 may be performed by control device 210. In some implementations, one or more process blocks of FIG. 6 may be performed by another device or a group of devices separate from or including control device 210, such as spectrometer 220.

As shown in FIG. 6, process 600 may include receiving information identifying results of a set of spectroscopic measurements performed on an unknown set (block 610). For example, control device 210 may receive information identifying the results of the set of spectroscopic measurements performed on the unknown set by spectrometer 220. The unknown set may include a set of samples (e.g., unknown samples) for which RMID is to be performed. For example, control device 210 may cause spectrometer 220 to perform the set of spectroscopic measurements on the set of samples, and may receive information identifying a set of spectra corresponding to the set of samples. In some implementations, control device 210 may receive the information identifying the results from multiple spectrometers 220. For example, control device 210 may cause multiple spectrometers 220 to perform the set of spectroscopic measurements on the unknown set (e.g., the same set of samples), and may receive information identifying a set of spectra corresponding to samples of the unknown set. Additionally, or alternatively, control device 210 may receive information identifying results of a set of spectroscopic measurements performed at multiple times, in multiple locations, or the like, and may classify a particular sample based on the set of spectroscopic measurements performed at the multiple times, in the multiple locations, or the like (e.g., based on averaging the set of spectroscopic measurements or based on another technique). In this way, control device 210 may account for physical conditions that may affect results of the set of spectroscopic measurements.

Additionally, or alternatively, control device 210 may cause a first spectrometer 220 to perform a first portion of the set of spectroscopic measurements on a first portion of the unknown set and may cause a second spectrometer 220 to perform a second portion of the set of spectroscopic measurements on a second portion of the unknown set. In this way, control device 210 may reduce a quantity of time to perform the set of spectroscopic measurements relative to causing all the spectroscopic measurements to be performed by a single spectrometer 220.

As further shown in FIG. 6, process 600 may include performing a first classification based on the results of the set of spectroscopic measurements and a global classification model (block 620). For example, control device 210 may perform the first classification based on the results and the global classification model. In some implementations, control device 210 may receive the global classification model for utilization in performing the first classification. For example, a first control device 210 may generate the global classification model (e.g., using an SVM-linear classifier and based on a set of spectroscopic measurements performed on a training set, as described herein with regard to FIG. 4), and may provide the global classification model to a second control device 210 for performing the first classification of the unknown set. Additionally, or alternatively, control device 210 may generate the global classification model (e.g., using the SVM-linear classifier and based on a set of spectroscopic measurements performed on a training set, as described herein with regard to FIG. 4), and may utilize the global classification model for performing the first classification of the unknown set.

In some implementations, control device 210 may assign a particular sample of the unknown set to a particular class, of a set of classes of the global classification model, when performing the first classification. For example, control device 210 may determine that a particular spectrum associated with the particular sample corresponds to a class of compounds (e.g., cellulose compounds, lactose compounds, caffeine compounds, etc.) based on the global classification model, and may assign the particular sample to the particular class. In some implementations, control device 210 may assign the particular sample based on a confidence metric. For example, control device 210 may determine, based on the global classification model, a probability that the particular spectrum is associated with each class of the global classification model. In this case, control device 210 may assign the particular sample to the particular class based on a particular probability for the particular class exceeding other probabilities associated with other classes. In this way, control device 210 determines a type of compound that the sample is associated with, thereby identifying the sample.

Additionally, or alternatively, control device 210 may determine another confidence metric associated with the first classification. For example, when control device 210 assigns a particular sample to a particular class when performing the first classification, control device 210 may determine a difference between the probability that the particular sample is associated with the particular class (e.g., termed a maximum probability) and another probability that the particular sample is associated with a next most likely class (e.g., termed a second maximum probability). In this way, control device 210 determines a confidence associated with assigning a particular sample to a particular class rather than a next most likely class. When the maximum probability and the second maximum probability are both relatively high and relatively similar (e.g., the maximum probability is 48% and the second maximum probability is 47% rather than the maximum probability being 48% and the second maximum probability being 4%), control device 210 provides a better indication of assignment accuracy by providing the difference between the maximum probability and the second maximum probability. In other words, in the first case of the maximum probability being 48% and the second maximum probability being 47%, assignment accuracy to the most likely class is relatively lower than in the second case of the maximum probability being 48% and the second maximum probability being 4%, although the maximum probability is the same for both cases. Providing a metric of the difference between the maximum probability and the second maximum probability can distinguish the two cases.

As further shown in FIG. 6, process 600 may include generating a local classification model based on the first classification (block 630). For example, control device 210 may generate the local classification model based on the first classification. The local classification model may refer to an in situ classification model generated using an SVM classification technique (e.g., SVM-rbf, SVM-linear, etc.; probability value based SVM, decision value based SVM, etc.; or the like) based on confidence metrics associated with the first classification. For example, when a set of confidence metrics are determined for a spectrum of a sample based on the global classification model, control device 210 may select a subset of classes of the global classification model based on respective probabilities that the spectrum is associated with each class of the global classification model. In this case, control device 210 may generate the local classification model using the SVM classification technique and based on the selected subset of classes.

In some implementations, an autoscaling pretreatment procedure may be performed. For example, to generate the local classification model, control device 210 may perform the autoscaling pretreatment procedure for the spectra associated with a subset of classes of the global classification model selected for the local classification model. In some implementations, the autoscaling pretreatment procedure may be performed for another classification, such as a first classification using the global classification model. In some implementations, another type of pretreatment procedure may be performed, such as a centering procedure, a transformation, or the like.

In some implementations, the subset of classes may include a threshold quantity of classes associated with the highest respective confidence metrics. For example, control device 210 may select ten classes of the global classification model based on the ten classes being associated with higher respective probabilities that the spectrum of the sample is associated therewith than with other classes of the global classification model, and may generate the local model based on the ten classes. In some implementations, control device 210 may select the subset of classes based on the subset of classes satisfying a threshold. For example, control device 210 may select each class that is associated with a probability satisfying the threshold. Additionally, or alternatively, control device 210 may select a threshold quantity of classes that each satisfy the threshold. For example, control device 210 may select up to ten classes provided that the ten classes each satisfy a minimum threshold probability. Additionally, or alternatively, control device 210 may select another quantity of classes (e.g., two classes, five classes, twenty classes, or the like).

In some implementations, control device 210 may generate multiple local classification models. For example, control device 210 may generate a first local classification model for a first spectrum of a first sample of the unknown set and a second local classification model for a second spectrum of a second sample of the unknown set. In this way, control device 210 may facilitate concurrent classification of multiple unknown samples by concurrently operating on the multiple unknown samples using the multiple local classification models.

In some implementations, control device 210 may generate a quantification model based on performing the first classification using the global classification model. For example, when control device 210 is being utilized to determine a concentration of a substance in an unknown sample, and multiple unknown samples are associated with different quantification models for determining the concentration of the substance, control device 210 may utilize the first classification to select a class for the unknown sample, and may select a local quantification model associated with the class of the unknown sample. In this way, control device 210 utilizes hierarchical classification and quantification models to improve raw material identification and/or quantification thereof.

As further shown in FIG. 6, process 600 may include performing a second classification based on the results of the set of spectroscopic measurements and the local classification model (block 640). For example, control device 210 may perform the second classification based on the results and the local classification model. In some implementations, control device 210 may perform the second classification for a particular spectrum. For example, control device 210 may assign the particular spectrum to a particular class based on the local classification model. In some implementations, control device 210 may determine a set of confidence metrics associated with the particular spectrum and the local classification model. For example, control device 210 may determine a probability that the particular spectrum is associated with each class of the local classification model, and may assign the particular spectrum (e.g., a particular sample associated with the particular spectrum) to a class with a higher probability than other classes of the local classification model. In this way, control device 210 identifies a sample of the unknown set.

Additionally, or alternatively, control device 210 may determine another confidence metric associated with the particular spectrum and the local classification model. For example, when control device 210 assigns a particular sample to a particular class when performing the second classification, control device 210 may determine a difference between the probability that the particular sample is associated with the particular class (e.g., a maximum probability) and another probability that the particular sample is associated with a next most likely class (e.g., a second maximum probability). In this way, control device 210 determines a confidence associated with assigning a particular sample to a particular class rather than a next most likely class when performing the second classification based on the local classification model.

In some implementations, control device 210 may perform multiple second classifications. For example, control device 210 may perform a second classification for a first spectrum associated with a first sample based on a first local classification model, and may perform another second classification for a second spectrum associated with a second sample based on a second local classification model. In this way, control device 210 facilitates concurrent classification of multiple samples of the unknown set. In some implementations, control device 210 may omit a portion of samples in the unknown set from the second classification. For example, when control device 210 determines a confidence metric for assigning a particular sample to a particular class based on the global classification model, and the confidence metric satisfies a threshold, control device 210 may omit the particular sample from second classification. In this way, control device 210 may reduce resource utilization relative to performing second classification for all samples of the unknown set.

In some implementations, control device 210 may perform a quantification after performing the first classification (and/or after performing the second classification). For example, control device 210 may select a local quantification model based on performing one or more classifications, and may perform a quantification relating to the particular sample based selecting the local quantification model. As an example, when performing raw material identification to determine a concentration of a particular chemical in a plant material, where the plant material is associated with multiple quantification models (e.g., relating to whether the plant is grown indoors or outdoors, in winter or in summer, or the like), control device 210 may perform a set of classifications to identify a particular quantification model. In this case, the control device 210 may determine that the plant is grown indoors in winter based on performing a set of classifications, and may select a quantification model relating to the plant being grown indoors in winter for determining the concentration of the particular chemical.

As further shown in FIG. 6, process 600 may include providing information identifying classifications for the unknown set based on performing the second classification (block 650). For example, control device 210 may provide information identifying a classification for a sample of the unknown set based on performing the second classification. In some implementations, control device 210 may provide information identifying a particular class for a particular sample. For example, control device 210 may provide information indicating that a particular spectrum associated with the particular sample is determined to be associated with the particular class, thereby identifying the sample. In some implementations, control device 210 may provide information indicating a confidence metric associated with assigning the particular sample to the particular class. For example, control device 210 may provide information identifying a probability that the particular sample is associated with the particular class, a difference between a maximum probability and a second maximum probability for the particular sample, or the like. In this way, control device 210 provides information indicating a likelihood that the particular spectrum was accurately assigned to the particular class.

In some implementations, control device 210 provides information identifying a class for multiple samples. For example, control device 210 may provide information indicating that a first sample of the unknown set is associated with a first class and a second sample of the unknown set is associated with a second class. In this way, control device 210 provides concurrent identification of multiple samples.

In some implementations, control device 210 may provide a quantification based on performing a set of classifications and a quantification. For example, based on identifying a local quantification model, control device 210 may provide information identifying a concentration of a substance in an unknown sample for which a set of classifications were utilized to select a quantification model for determining the concentration of the substance.

In some implementations, control device 210 may provide an output relating to a class of a sample. For example, control device 210 may provide a binary output (e.g., a yes/no output) relating to a classification of an unknown sample for which a first set of classes correspond to a first binary output (e.g., yes) and a second set of classes correspond to a second binary output (e.g., no) based on classifying the unknown sample into one of the first set of classes or the second set of classes. As an example, for a first set of classes (e.g., Kosher Meat, which may include Kosher Beef Strip Steak, Kosher Beef Ribs, Kosher Chicken Thighs, Kosher Chicken Breasts, etc.) and a second set of classes (e.g., Non-Kosher Meat, which may include Non-Kosher Beef Ribs, Non-Kosher Pork, Non-Kosher Chicken Wings, etc.), control device 210 may provide an output of Kosher or Non-Kosher based on classifying an unknown sample into a particular class of the first set of classes or the second set of classes. As another example, control device 210 may utilize a set of classes relating to food being classified as Halal or non-Halal, and may provide an output indicating whether a sample corresponds to a Halal classification or a non-Halal classification (i.e., whether an animal from which the sample was derived was slaughtered in a Halal manner, regardless of whether other criteria for Halal classification are met, such as religious certification, prayer during slaughter, or the like). In this way, control device 210 may provide a classification with a greater likelihood of accuracy relative to providing an identification of a particular class when the identification of the particular class is not important to the user of control device 210 (e.g., a person attempting to determine whether an item of meat is Kosher, rather than attempting to determine the type of meat).

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7A:
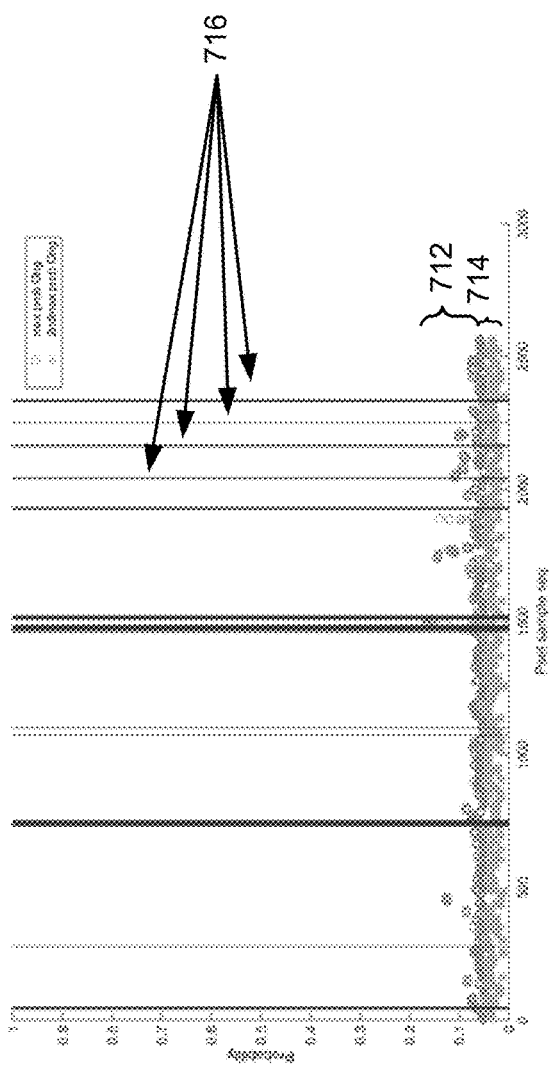
FIGS. 7A and 7B are diagrams of an example implementation relating to a prediction success rate associated with the example process shown in FIG. 6.
Figure 7A:
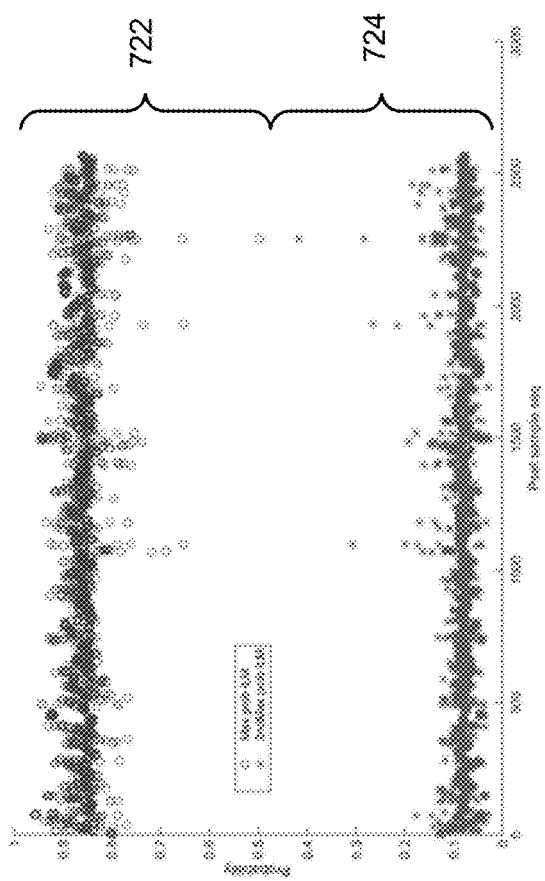
Figure 7B:
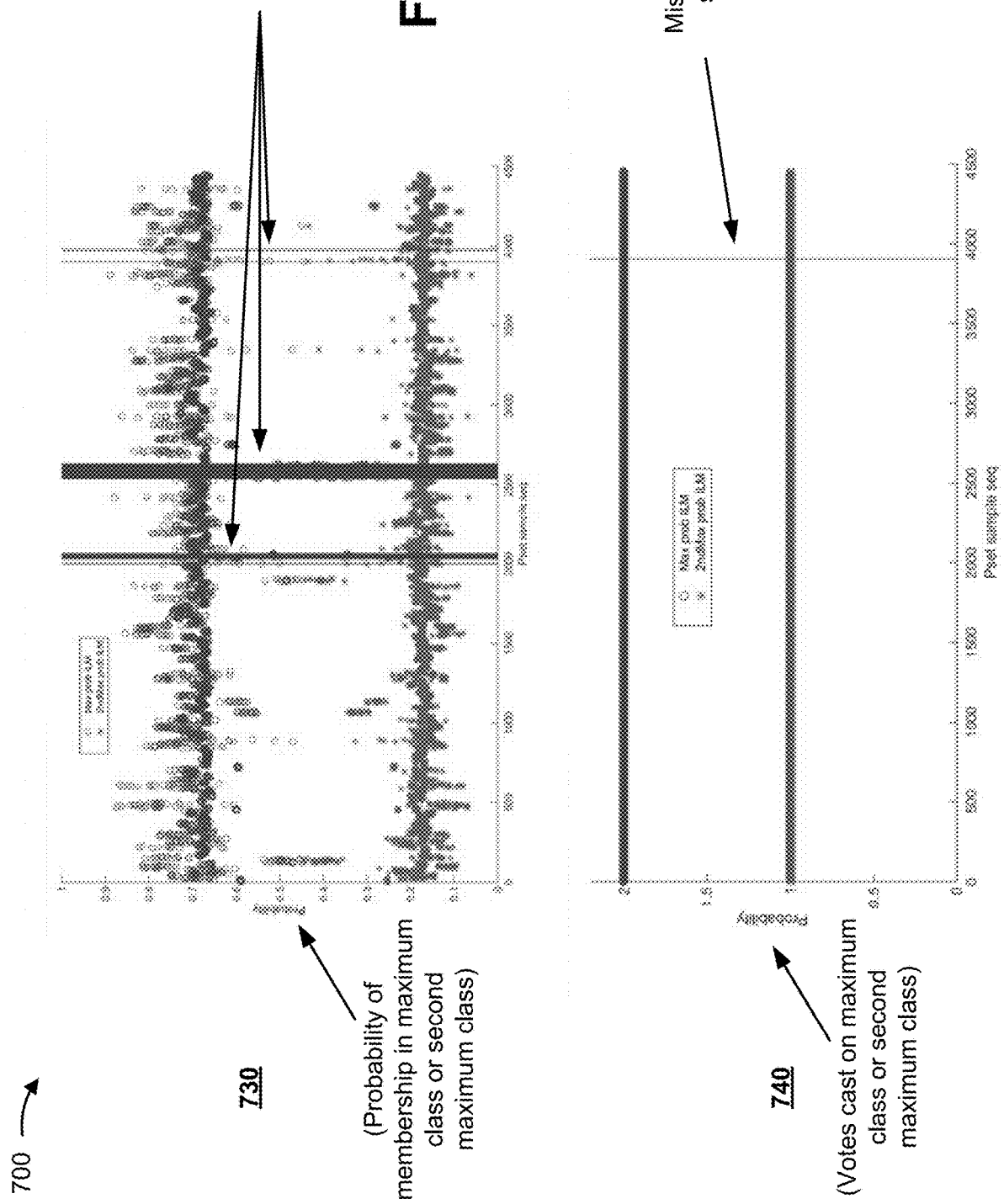

FIGS. 7A and 7B are diagrams of an example implementation 700 relating to prediction success rates associated with example process 600 shown in FIG. 6. FIGS. 7A and 7B show example results of raw material identification using a hierarchical support vector machine (hier-SVM-linear) based technique.

As shown in FIG. 7A, and by reference number 710, a set of confidence metrics are provided for an unknown set. For each sample of the unknown set, control device 210 determines a probability that the sample is associated with each class of the global classification model. A maximum probability is compared with a second maximum (a next-maximum) probability for each sample of the unknown set. As shown by reference number 712, maximum probabilities for the unknown set range from approximately 5% to approximately 20%. As shown by reference number 714, second maximum probabilities for the unknown set range from approximately 0% to approximately 5%. As shown by reference number 716, samples of the unknown set that control device 210 incorrectly classified based on the global classification model are highlighted (e.g., 84 samples of 2645 samples in the unknown set are incorrectly classified).

As further shown in FIG. 7A, and by reference number 720, a set of confidence metrics are provided for the unknown set. For each sample of the unknown set, control device 210 determines a probability that the sample is associated with each class of a corresponding local classification model. The maximum probability is compared with the second maximum (a next-maximum) probability for each sample of the unknown set. As shown by reference number 722, maximum probabilities for the unknown set range from approximately 50% to approximately 98%. As shown by reference number 724, second maximum probabilities for the unknown set range from approximately 2% to approximately 45%. Moreover, the probability difference between the maximum probability and the second maximum probability is greater than approximately 0.33 (33%) for each sample of the unknown set except for one sample (for which the probability difference is approximately 8% and for which a correct classification was nonetheless performed). Based on performing a set of classifications, control device 210 correctly classifies all members of the unknown set.

With regard to FIG. 7B, when a quantity of samples in each class of a classification model (e.g., a global classification model, a local classification model, etc.) fails to satisfy a threshold, control device 210 may determine reduced confidence metrics and associated prediction accuracy when assigning samples of an unknown set to classes. As shown by reference number 730, when the quantity of samples in each class does not satisfy the threshold, control device 210 misclassifies 128 samples out of 4451 samples after performing first classification based on a global classification model and second classification based on a set of local classification models (e.g., a probability based SVM classifier local classification models) for the unknown set.

As shown by reference number 740, when control device 210 performs another first classification based on the global classification model and another second classification based on another set of local classification models (e.g., decision value based SVM classifier local classification models), control device 210 misclassifies 1 sample out of 4451 samples. In this way, control device 210 utilizes a decision value based SVM classifier to improve classification accuracy relative to a probability based SVM classifier.

As indicated above, FIGS. 7A and 7B are provided merely as an example. Other examples are possible and may differ from what was described with regard to FIGS. 7A and 7B.

Figure 8A:
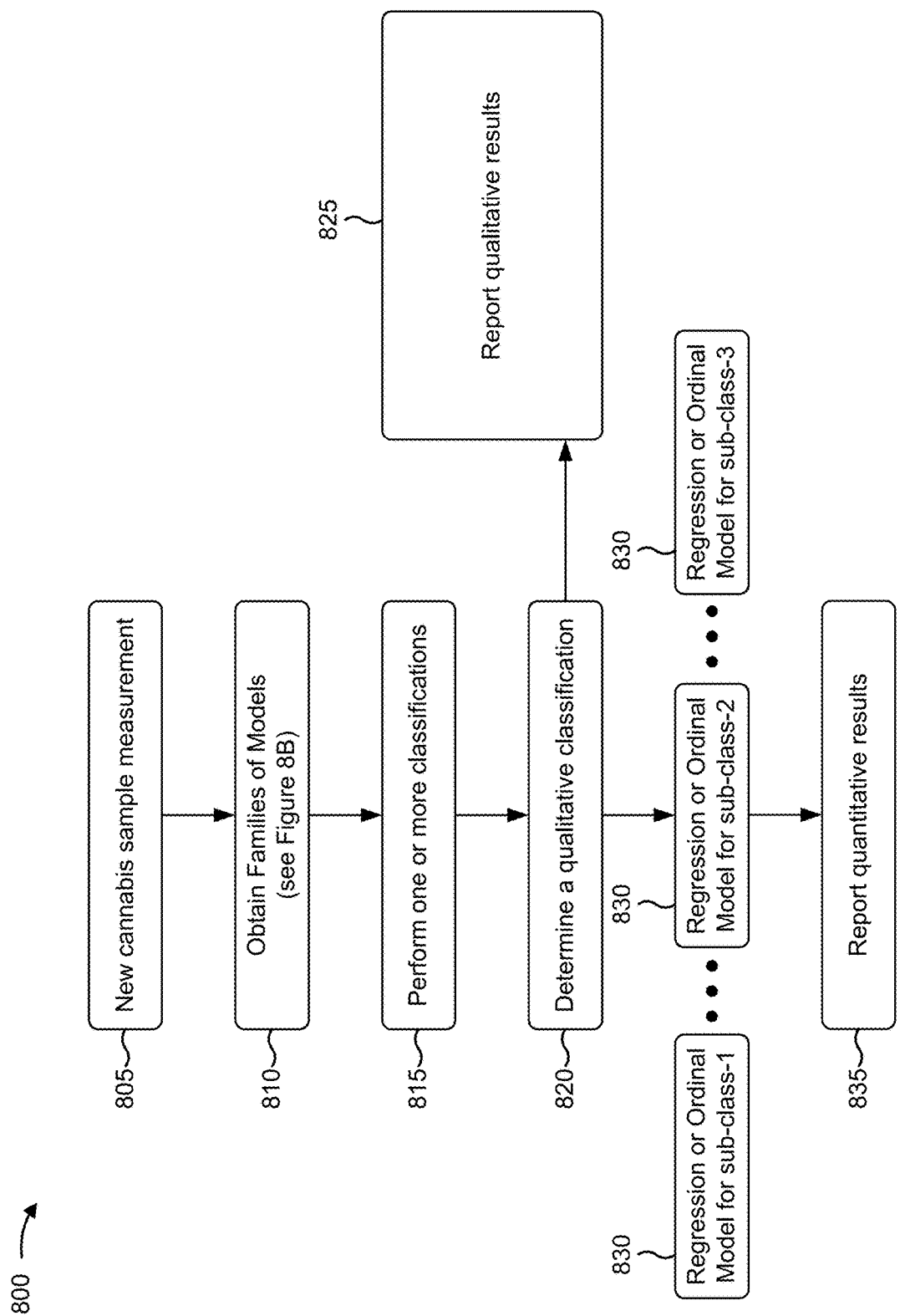
FIGS. 8A and 8B are diagrams of an example implementation relating to the example process shown in FIG. 6.
Figure 8B:
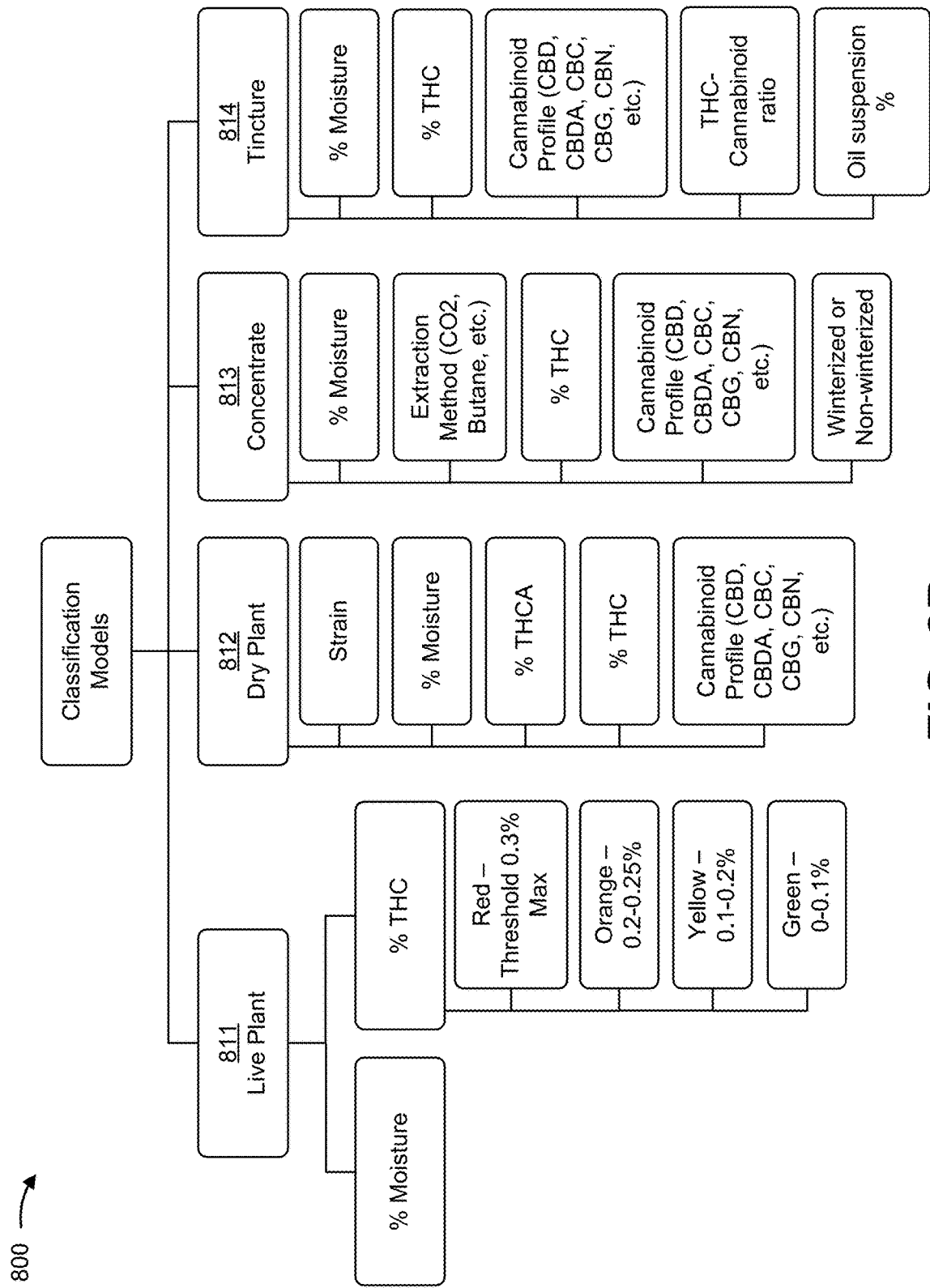

FIGS. 8A and 8B are diagrams of an example implementation 800 relating to example process 600 shown in FIG. 6. FIGS. 8A and 8B show an example relating to utilizing a classification and a quantification technique.

With regard to FIGS. 8A and 8B and other example implementations described herein, a regulation may require that tetrahydrocannanbinol (THC) content in commercially grown hemp not exceed a threshold (e.g., 0.3%), and may require a grower to destroy a crop that exceeds the threshold. A laboratory test technique may be associated with an excessive turnaround time (e.g., 7 to 10 days), which may result in plant THC content changing from acceptable (e.g., at a time of sampling) to unacceptable (e.g., at a time of test results). Thus, a grower may utilize spectrometer 220 to perform a spectroscopic measurement of the cannabis sample to determine a THC content or another characteristic with a reduced amount of time relative to the laboratory test technique.

In this case, utilizing a local classification model may improve accuracy, as environment conditions, plant genetics, or the like may result in different quantification models being associated with different classes of plants. For example, a cannabis plant grown indoors may be associated with a first regression model to determine THC content and a cannabis plant grown outdoors may be associated with a second regression model to determine THC content. The grower may utilize spectrometer 220 and control device 210 to determine a class of the cannabis plant, select a quantification model for quantifying a characteristic of the cannabis plant (e.g., THC content), and may utilize the quantification model to quantify the characteristic, as described herein.

As shown in FIG. 8A, and by reference number 805, control device 210 may receive a spectroscopic measurement for a cannabis sample. As shown in FIG. 8A, and by reference number 810, and in more detail in FIG. 8B, control device 210 may obtain, from a data structure, stored information identifying a set of potential classes for the cannabis sample and a set of models (e.g., classification models or quantification models) for classifying and/or quantifying the cannabis sample based on a class to which the cannabis sample is assigned.

As shown in FIG. 8B, and by reference numbers 811-814, control device 210 may receive information identifying a set of classification models or quantification models relating to a set of potential classes for the cannabis sample. For example, control device 210 may receive information identifying a group of quantification models for a sample obtained from a live plant class, such as a moisture percentage or a THC percentage quantification model (e.g., a set of THC percentage quantification models relating to determining whether a threshold THC percentage is satisfied, such as satisfying a red threshold indicating forbidden, a green threshold indicating acceptable, or the like). In some implementations, control device 210 may receive a classification model for determining whether a threshold percentage of THC content is present (e.g., a red threshold classification model, a green threshold classification model, or the like), and may receive a particular type of quantification model (e.g., an ordinal model) for quantifying the THC content present at the threshold level with a greater accuracy than a quantification model associated with quantifying any THC content.

Additionally, or alternatively, control device 210 may obtain a classification model for a dry plant class, such as a strain classification model, or a quantification model for a dry plant class, such as a moisture percentage, a THC acid (THCA) percentage, a THC percentage, or a relative cannabinoid profile (e.g., a relative percentage of cannabidiol (CBD), CBD acid (CBDA), cannabichromene (CBC), cannabigerol (CBG), cannabinol (CBN), or the like) quantification model. Additionally, or alternatively, control device 210 may obtain a classification model for a concentrate class, such as an extraction method or winterization classification model, or a quantification model for a concentrate, such as a moisture percentage, a THC percentage, or a cannabinoid profile quantification model. Additionally, or alternatively, control device 210 may obtain a quantification model for a tincture, such as a moisture percentage, a THC percentage, a cannabinoid profile, a cannabinoid ratio, or an oil suspension percentage quantification model.

Returning to FIG. 8A, and as shown by reference number 815, control device 210 may utilize one or more classifications (e.g., a global classification model and/or a local classification model) to perform a qualitative classification of the cannabis sample using one or more of the classification models 811-814. As shown by reference number 820, control device 210 may determine a classification of the cannabis sample based on performing the qualitative classification of the cannabis sample. As shown by reference number 825, control device 210 may provide information identifying one or more qualitative results relating to the cannabis sample, such as an extraction method classification, a strain classification, or the like. As shown by reference numbers 830, control device 210 may utilize one or more quantification models (e.g., a regression model, an ordinal model, or the like) related to the qualitative results, such as a moisture percentage quantification model relating to one or more sub-classes of a strain (e.g., a most likely sub-class, a second most likely sub-class, or the like) determined using a strain classification model, to perform a quantitative analysis of the cannabis sample. As shown by reference number 835, control device 210 may provide results of the quantitative analysis of the cannabis sample. In this way, control device 210 and spectrometer 220 enable rapid classification and quantification relating to cannabis samples and/or another type of sample.

As indicated above, FIGS. 8A and 8B are provided merely as an example. Other examples are possible and may differ from what was described with regard to FIGS. 8A and 8B.

In this way, control device 210 utilizes a global classification model and a local classification model generated based on the global classification model to perform RMID.

The foregoing disclosure provides illustration and description, but is not intended to be exhaustive or to limit the implementations to the precise form disclosed. Modifications and variations are possible in light of the above disclosure or may be acquired from practice of the implementations.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method comprising:
generating, by a first device, a global classification model;
determining, by the first device, that the global classification model satisfies a verification threshold; and
providing, by the first device and based on determining that the global classification model satisfies the verification threshold, the global classification model to a second device associated with a first spectrometer and to a third device associated with a second spectrometer.

2. The method of claim 1, further comprising:
selecting a hier-support vector machine (SVM)-linear classifier for generating the global classification model.

3. The method of claim 2, further comprising:
testing the hier-SVM-linear classifier against one or more other classifiers,
wherein selecting the hier-SVM-linear classifier comprises:
selecting the hier-SVM-linear classifier based on testing the hier-SVM-linear classifier against the one or more other classifiers.

4. The method of claim 1, wherein determining that the global classification model satisfies the verification threshold comprises:
determining that the global classification model has an accuracy that exceeds the verification threshold.

5. The method of claim 1, wherein the global classification model is utilized when performing raw material identification (RMID) on spectroscopic measurements performed by the first spectrometer.

6. The method of claim 1, further comprising:
receiving information identifying results of a set of spectroscopic measurements,
wherein generating the global classification model comprises:
generating the global classification model based on the information identifying the results of the set of spectroscopic measurements.

7. The method of claim 6, wherein the information identifying the results of the set of spectroscopic measurements is received from multiple spectrometers.

8. A first device, comprising:
one or more memories; and
one or more processors communicatively coupled to the one or more memories, configured to:
generate a global classification model;
determine that the global classification model satisfies a verification threshold; and
provide, based on determining that the global classification model satisfies the verification threshold, the global classification model to a second device associated with a first spectrometer to a third device associated with a second spectrometer.

9. The first device of claim 8, wherein the one or more processors are further configured to:
select a hier-support vector machine (SVM)-linear classifier for generating the global classification model.

10. The first device of claim 9, wherein the one or more processors are further configured to:
test the hier-SVM-linear classifier against one or more other classifiers,
wherein selecting the hier-SVM-linear classifier comprises:
select the hier-SVM-linear classifier based on testing the hier-SVM-linear classifier against the one or more other classifiers.

11. The first device of claim 8, where, when determining that the global classification model satisfies the verification threshold, the one or more processors are further configured to:
determine that the global classification model has an accuracy that exceeds the verification threshold.

12. The first device of claim 8, wherein the global classification model is utilized when performing raw material identification (RMID) on spectroscopic measurements performed by the first spectrometer.

13. The first device of claim 8, wherein the one or more processors are further configured to:
receive information identifying results of a set of spectroscopic measurements,
where, when generating the global classification model, the one or more processors are configured to:
generate the global classification model based on the information identifying the results of the set of spectroscopic measurements.

14. The first device of claim 13, wherein the information identifying the results of the set of spectroscopic measurements is received from multiple spectrometers.

15. The first device of claim 8, wherein the first device is associated with a third spectrometer that is separate from the first spectrometer and the second spectrometer.

16. A non-transitory computer-readable medium storing instructions, the instructions comprising:
one or more instructions that, when executed by one or more processors of a first device, cause the one or more processors to:
generate a global classification model;
determine that the global classification model satisfies a verification threshold; and
provide, based on determining that the global classification model satisfies the verification threshold, the global classification model to a second device associated with a first spectrometer and to a third device associated with a second spectrometer.

17. The non-transitory computer-readable medium of claim 16, wherein the one or more instructions, when executed by the one or more processors, further cause the one or more processors to:
select a hier-support vector machine (SVM)-linear classifier for generating the global classification model.

18. The non-transitory computer-readable medium of claim 17, wherein the one or more instructions, when executed by the one or more processors, further cause the one or more processors to:
test the hier-SVM-linear classifier against one or more other classifiers,
wherein the hier-SVM-linear classifier is selected based on testing the hier-SVM-linear classifier against the one or more other classifiers.

19. The non-transitory computer-readable medium of claim 16, wherein the one or more instructions to determine that the global classification model satisfies the verification threshold comprise:
one or more instructions to determine that the global classification model has an accuracy that exceeds the verification threshold.

20. The non-transitory computer-readable medium of claim 16, wherein the global classification model is utilized when performing raw material identification (RMID) on spectroscopic measurements performed by the first spectrometer.

21. The non-transitory computer-readable medium of claim 16, wherein the one or more instructions, when executed by the one or more processors, further cause the one or more processors to:
receive information identifying results of a set of spectroscopic measurements,
wherein the one or more instructions to generate the global classification model comprise:
one or more instructions to generate the global classification model based on the information identifying the results of the set of spectroscopic measurements.

* * * * *